United States Patent [19]

Elek et al.

[11] Patent Number: 4,626,533

[45] Date of Patent: Dec. 2, 1986

[54] 7-(2-THIENYLACETAMIDO)-3-ACYLAMINOMETHYL-CEPHALOSPORINS

[75] Inventors: Sándor Elek; Ildikó Mihók née Borbély; Miklós Mihók, all of Debrecen, Hungary

[73] Assignee: Biogal Gyogyszergyar, Debrecen, Hungary

[21] Appl. No.: 689,056

[22] PCT Filed: Apr. 19, 1984

[86] PCT No.: PCT/HU84/00026

§ 371 Date: Dec. 7, 1984

§ 102(e) Date: Dec. 7, 1984

[87] PCT Pub. No.: WO84/04096

PCT Pub. Date: Oct. 25, 1984

[30] Foreign Application Priority Data

Apr. 19, 1983 [HU] Hungary ............................ 1351/83

[51] Int. Cl.$^4$ .................. A61K 31/545; C07D 501/46
[52] U.S. Cl. ...................................... 514/202; 540/222
[58] Field of Search ........................... 544/22; 514/202

[56] References Cited

U.S. PATENT DOCUMENTS 3,274,186  9/1966  Barker .................................... 544/16
3,728,342  4/1973  Kukolja .................................. 544/22
3,887,549  6/1975  Christensen ........................... 544/22
4,258,040  3/1981  Christensen ........................... 544/21

FOREIGN PATENT DOCUMENTS 25187  3/1981  Japan ..................................... 544/22

OTHER PUBLICATIONS

Toyama (11/4/81) Derwent Abstract 92195.
Dunn, J. of Antimicrobial Chemotherapy (1982) 10, Suppl. C., 1-10.

Primary Examiner—Sidney Marantz
Assistant Examiner—Robert Benson
Attorney, Agent, or Firm—Karl F. Ross; Herbert Dubno

[57] ABSTRACT

The invention relates to novel compounds of the formula:

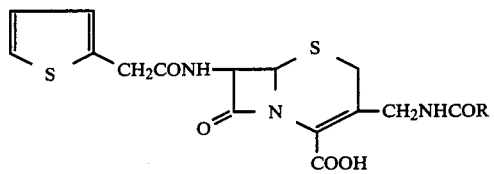

where R=4-chlorophenylmethyl or 2,6-dichlorophenylmethyl or an alkalimetal salt thereof.

The compounds have utility as antibiotics.

2 Claims, No Drawings

7-(2-THIENYLACETAMIDO)-3-ACYLAMINOMETHYL-CEPHALOSPORINS

TECHNICAL FIELD

The present invention is directed to novel cephalosporins of the formula (I), a process for their preparation, the pharmaceutical compositions containing compounds of the formula (I) as active ingredients and their use in therapy as antibiotics.

BACKGROUND OF THE INVENTION

The antibiotics of the cephalosporin-type play a prominent role in the treatment of human infectious diseases. Thus, e.g. Cephalotine, Cephaloglycine, Cephazoline and Cephalexine (c.f. Belgian patent specification No. 618,663; British patent specification No. 985,747; U.S. Pat. No. 3,516,997; Belgian patent specification No. 696,026, respectively) are widely known, valuable cephalosporin derivatives possessing antibacterial activity.

Presently great efforts are being made in order to prepare novel antibiotics suitable for the treatment of different infectious diseases.

Originally the semisynthetic cephalosporin derivatives were prepared by acylating the 7-amino group of 7-amino-cephalosporanic acid (further referred to as 7-ACA), but the later extensive experiments enabled the preparation of novel derivatives by changing the substituents in the positions 7 and/or 3 of the cephalosporin ring as well (Fortschritte der Chemie Organischer Naturstoff, 28, p. 343–403 (1970)).

A great number of cephalosporin derivatives as well as pharmaceutical compositions have been prepared up to now. Numerous scientific publications, technical books and patents relating to this subject are known (e.g. Flynn, E. H.: "Cephalosporin and Pennicillins", Academic Press, New York and London, 1972; Perlman, D.: "Structure-activity Relationship Among the Semisynthetic Antibiotics", New York, 1977; O'Callaghan, C. H.: Antimicrob. Chemother. 5, 635 (1979)).

SUMMARY OF THE INVENTION

The invention is directed to novel cephalosporins of the formula (I) and the pharmaceutically acceptable salts thereof

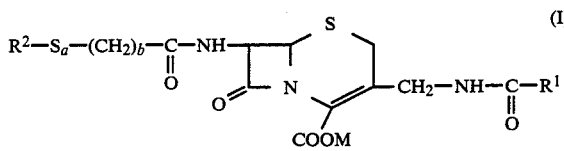

wherein
$R^1$ is $C_{1-4}$ alkyl; $C_{2-4}$ alkenyl; phenyl; benzyl; phenyl substituted by one or more different or the same halo atom(s); or benzyl substituted by one or more different or the same halo atom(s);
M is hydrogen or an alkaline metal,
$R^2$ is 3-phenyl-5-methylisoxazol-4-yl if $a=0$ and $b=0$; 2-thienyl if $a=0$ and $b=1$; halo if $a=0$ and $b=1, 2, 3$ and 4; and tetrazolyl, thiadiazolyl, thiazolyl, oxadiazolyl, oxazolyl, triazolyl, imidazolyl, pyrimidinyl, triazinyl or thiatriazolyl, all these groups being optionally substituted by halo, amino, nitro, alkyl, alkoxy, aryl, aralkyl, alkylamino, thioalkyl, furyl or thienyl if $a=1$ and $b=1$, a process for their preparation, pharmaceutical compositions containing the same and their use as antibiotics.

The antibiotics according to the invention have not only a much broader spectrum of efficiency than the penicillins because the new compounds are effective not only against Gram-positive bacteria but they are effective against most Gram-negative bacteria as well and in vitro they are also stable against β-lactamases produced by different microorganism strains.

The compounds of the formula (I) according to the invention structurally differ from the known cephalosporin derivatives in the feature that they comprise an acylaminomethyl group in position 3 of the dihydrothiazine moiety. The Japanese published patent application No. 56-140997 includes a method for the preparation of 7-amino-3-(substituted)methylceph-3-em-4-carboxylic acids of similar structure.

DETAILED DESCRIPTION OF THE INVENTION

The compounds of the formula (I) according to the invention are prepared by reacting a compound of the formula (I)

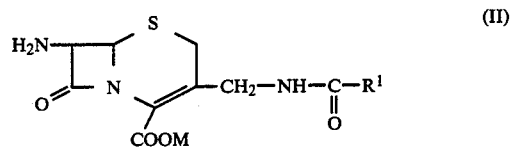

wherein $R^1$ and M are the same as set forth above, with an appropriately substituted isoxazole-carbonyl chloride, 2-thienylacetyl chloride or with a compound of the formula (III)

in which formula X is a halo atom and b is equal to 1, 2, 3 or 4, in a mixture of water and an organic solvent, preferably in aqueous acetone, in the presence of an alkaline metal hydroxide as acid binding agent, at a pH 7 to 8 at a temperature of 0° to 40° C., preferably 0° to 10° C. After the reaction is accomplished, the products of the formula (I) are separated by known techniques, e.g. by evaporation of the solvent, addition of water, extraction with water inmiscible organic solvent in an acidic medium.

As an alternative method for the preparation of the products of the formula (I) the compounds of the formula (IV),

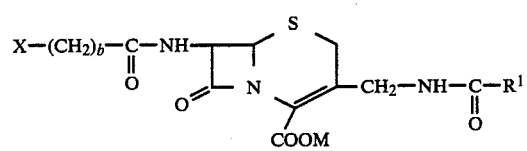

wherein $R^1$, M, X and b are as defined hereinabove, forming a narrower group of the compounds of the formula (I) and being prepared by the aid of the acid halides of the formula (III), are reacted with a heteroarylthiol of the formula

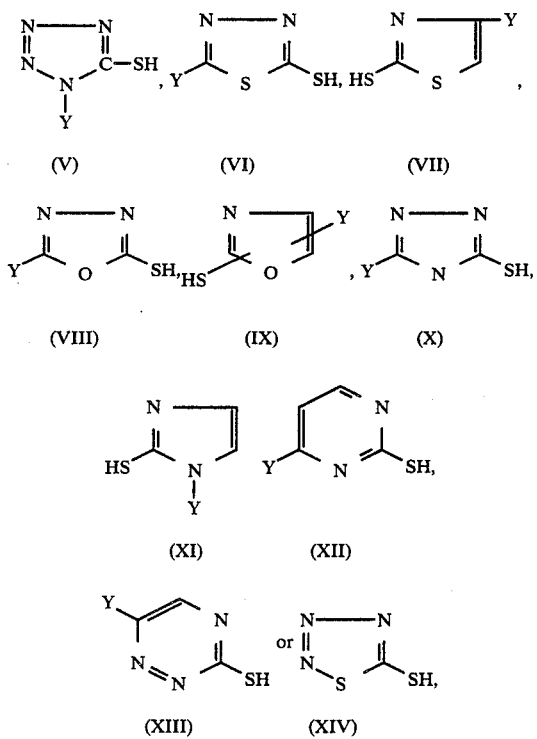

in which formulae Y represents a halo, amino, nitro, alkyl, alkoxy, aryl, aralkyl, alkylamino, thioalkyl, furyl or thienyl group.

The compounds of the formula (IV) and the heteroaryl thiols of the above formulae are employed in a substantially equivalent amount. The salts of the thiols preferably employed in this reaction can be prepared by methods known per se, e.g. by means of alkaline metal carbonates, e.g. sodium carbonate, potassium carbonate or similar compounds. If the metal salts of the thiols are used, the reaction is carried out in the presence of water or a water-miscible organic solvent, e.g. dioxane, tetrahydrofuran, methanol, ethanol or, preferably, acetone. The reaction is conducted at room temperature in a weakly basic medium, and a base, e.g. sodium hydrocarbonate, potassium carbonate or triethyl amine is used as acid-binding agent. If the reactants' decomposition is expected under the conditions of the reaction, the reaction is carried out in an anhydrous medium and/or at low temperature.

According to an especially preferred embodiment of the process of the invention the starting materials are used in the form of a free acid, and the reaction is carried out in a neutral medium, e.g. anhydrous acetone or anhydrous dimethyl formamide, in the presence of an alkaline metal carbonate, e.g. potassium carbonate, as acid-binding agent.

After the reaction is accomplished the compounds of the formula (I) prepared as described hereinabove are separated from the reaction mixture by methods known per se, e.g. by solvent change, evaporation of the solvent, extraction with a water-inmiscible organic solvent in acidic medium. The crude products can further be purified by methods known per se e.g. by recrystallization, chromatography or similar methods.

The invention further relates to pharmaceutical compositions comprising as active ingredient a compound of the formula (I) or a pharmaceutically acceptable salt thereof in association with at least one organic or inorganic, solid or liquid pharmaceutically acceptable adjuvant being suitable e.g. for oral or parenteral administration. The pharmaceutical compositions may be presented in solid unit dosage forms, e.g. in the form of tablets or capsules, or in solutions, suspensions or emulsions. The pharmaceutical compositions can also contain such excipients as e.g. protecting agents, stabilizing agents, wetting agents, emulgeating agents or buffers.

Table I contains the MIC values of the most effective compounds according to the invention.

TABLE I

| Compound prepared according to Example | Gram-positive strains MIC value (μg./ml.) | Gram-negative strains MIC value (μg./ml.) |
| --- | --- | --- |
| 5  | 0.06 → 100  | 50 → 100 |
| 6  | 0.004 → 10  | 25 → 100 |
| 8  | 0.03 → 10   | >100 |
| 14 | 0.03 → 10   | >100 |
| 15 | 0.03 → 10   | >100 |

The examinations were carried out by using the bacteria strains listed hereinbelow:

Gram-positive strains

S. aureus 112002
S. aureus 112003
S. epidermidis 110001
S. faecalis 80171

Gram-negative strains

E. coli 35034
Klebsiella 52001
Klebsiella ATCC 1200
S. hartford 10063
P. mirabilis 60012
P. morganii 63002
P. rettgeri 65002
P. inconstans 67001
P. aeruginosa ATCC 27853

The invention is illustrated by the following, non-limiting examples.

The following methods were employed in the course of the determination of the identifying data given in the examples:

The melting points were determined by a Thiele device. The thin-layer chromatography examinations were carried out by using a DC Alufolien Kieselgel 60 F254 adsorbent and acetone/acetic acid (95:5) /$R_f^1$/ or benzene/methanol (1:1) /$R_f^2$/ eluent. The IR spectra were measured by an UNICAM SP 200 G spectrophotometer and the NMR spectra were measured by a BRUKER WP 200 SY instrument.

EXAMPLE 1

2.72 g. of 7-aminocephalosporanic acid (7-ACA) were suspended in 15 ml. of anhydrous acetonitrile and 5.68 g. of boron trifluoride etherate were added. The reaction mixture was stirred at 40° C. for 5 hours. The solvent was evaporated in vacuo and the residue as taken up with 30 ml. of water. The pH of the solution was adjusted to 3.5 by adding about 10 ml. of a 25% aqueous sodium hydroxide solution and the precipitate separated (the unreacted 7-ACA) was filtered off. The pH of the mixture was adjusted to 7 by adding potassium phosphate solution, thereafter the mixture was diluted with 10 ml. of acetone. 2.4 g. (0.015 moles) of 2-thienylacetyl chloride dissolved in 4 ml. of anhydrous acetone were added to the mixture dropwise at 0° to 5° C. and during the addition the pH of the mixture was maintained between 7 and 8. After the mixture had been stirred for a further hour at room temperature at a pH of 7 to 8 the reaction was accomplished. The pH of the reaction mixture was adjusted to 5 by adding some diluted sulphuric acid, and then the solution was extracted with 30 ml. of ethyl acetate. The pH of the aqueous phase was adjusted to 2 by adding some diluted sulphuric acid and the mixture was extracted with 60 ml. of ethyl acetate. The organic extract was dried over magnesium sulphate. The solvent was evaporated in vacuo, the residue was treated with ether, filtered and washed. 2.76 g. of 7-(2-thienyl)acetylamino-3-acetylaminomethylceph-3-em-4-carboxylic acid were obtained in powder form.

The product was dissolved in 20 ml. of anhydrous acetone and an equimolar amount of sodium acetate dissolved in anhydrous methanol was added. The substance separated was recovered by filtration, washed with ether and dried in vacuo.

M.p.: 168°–172° C. (with decomposition)
$R_f^1$: 0.35[1]
$^1$H-NMR: ($\delta$ ppm) DMSO-$d_6$: 2.08 (s, 3H, CH$_3$CO); 3.64 (ABq, 2H, H-2); 3.96 (s, 2H, CH$_2$CO); 4.26 (ABdq, 2H, H-10); 5.20 (d, 1H, H-6); 5.84 (Q, 1H, H-7); 7.08–7.48 (m, 3H, H—Ar); 8.26 (t, 1H, C$^{10}$—NH); 9.26 (d, 1H, C$^7$—NH).
Yield: 70%.

EXAMPLE 2

2.72 g. of 7-ACA were dissolved in 19 ml. of trifluoroacetic acid, then 5.68 g. of boron trifluoride ethereate and 0.74 g. of acrylnitrile were added. The reaction mixture was stirred at 40° C. for 4 hours. Then the method disclosed in Example 1 was followed. 2.4 g. of 7-(2-thienyl)acetylamino-3-acroylaminomethylceph-3-em-carboxylic acid were obtained in powder form.

M.p.: 182°–185° C. (decomp.)
$R_f^2$: 0.51
$^1$H-NMR ($\delta$ ppm) DMSO-$d_6$: 3.17 (ABq, 2H, H-2); 3.75 (s, 2H, CH$_2$CO); 4.06 (ABdq, 2H, H-10); 4.88 (d, 1H-H-6); 5.45 (q, 1H, H-7); 5.53–6.36 (m, 3H, —CH=CH$_2$); 6.92–7.37 (m, 3H, H—Ar); 8.17 (t, 1H, C$^{10}$—NH); 8.95 (d, 1H, C$^7$—NH).
Yield: 59%.

EXAMPLE 3

The method of Example 1 was followed with the difference that 3.56 g. of 3-phenyl-5-methylisoxazole-4-carbonyl chloride were employed.

3.09 g. of 7-(3-phenyl-5-methyl-isoxazole-4-yl)carboxamido-3-acetylaminomethyl-ceph-3-em-carboxylic acid were obtained. The product was dissolved in 25 ml. of anhydrous acetone and an equivalent amount of sodium acetate dissolved in anhydrous methanol was added. The substance separated was filtered, washed with ether and dried in vacuo.

Weight: 2.6 g.
M.p.: 170°–174° C. (decomp.)
$R_f^1$: 0.26
$^1$H-NMR ($\delta$ ppm) DMSO-$d_6$: 1.90 (s, 3H, CH$_3$CO); 2.60 (s, 3H, CH$_3$); 3.50 (ABq, 2H, H-2); 4.11 (ABdq, 2H, H-10); 5.20 (d, 1H, H-6); 5.83 (q, 1H, H-7); 7.50–7.73 (m, 5H, H—Ar); 8.16 (t, 1H, C$^{10}$—NH); 9.53 (d, 1H—C$^7$—NH).
Yield: 67%.

EXAMPLE 4

The method described in Example 2 was followed with the difference that 3.56 g. of 3-phenyl-5-methylisoxazole-4-carbonyl chloride were used. 2.63 g. of 7-(3-phenyl-5-methyl-isoxazole-4-yl)-carboxamido-3-acryloxylaminomethylceph-3-em-4-carboxylic acid were recovered.

$^1$H-NMR ($\delta$ ppm) DMSO-$d_6$: 2.60 (s, 3H, CH$_3$); 3.17 (ABq, 2H, H-2); 4.06 (ABdq, 2H-H-10); 5,20 (d, 1H, H-6); 5,83 (q, 1H, H-7); 5.53–6.36 (m, 3H, —CH=CH$_2$); 7.50–7.73 (m, 5H, H—Ar); 8.17 (t, 1H, C$^{10}$—NH); 8.95 (d, 1H, C$^7$—NH).
Yield: 56%.

EXAMPLE 5

2.72 g. of 7-ACA were dissolved in 19 ml. of trifluoroacetic acid, then 5.68 g. of boron trifluoride etherate and 2.12 g. of 4-cyanomethylchlorobenzene were added. The reaction mixture was stirred at 40° C. for 4 hours. The further steps were the same as in Example 1. Thus, 3.13 g. of 7-(2-thienyl)-acetylamino-3-(4-chlorophenylacetylamino)methylceph-3-em-4-carboxylic acid were obtained.

M.p.: 119°–123° C. (decomp.)
$R_f^2$: 0.46
$^1$H-NMR ($\delta$ ppm) DMSO-$d_6$: 3.40 (ABq, 2H, H-2), 3.47 (s, 2H, —COCH$_2$—); 3.77 (s, 2H, —CH$_2$CO—); 4.07 (ABdq, 2H, H-10); 5.03 (d, 1H, H-6); 5.67 (q, 1H, H-7); 6.92–7.37 (m, 7H, H—Ar); 8.32 (t, 1H, C$^{10}$—NH); 9.14 (d, 1H, C$^7$—NH).
Yield: 62%.

EXAMPLE 6

2.72 g. of 7-ACA were dissolved in 19 ml. of trifluoroacetic acid, then 5.68 g. of boron trifluoride etherate and 2.4 g. of 2,6-dichlorobenzoyl nitrile were added. The reaction mixture was stirred at 50° C. for 15 hours. The further steps were the same as in Example 1. Thus 3.42 g. of 7-(2-thienyl)acetylamino-3-(2,6-dichlorobenzoylamino)-methylceph-3-em-4-carboxylic acid were obtained.

M.p.: 183°–185° C. (decomp.)
$R_f^1$: 0.6
$^1$H-NMR ($\delta$ ppm) DMSO-$d_6$: 3.45 (ABq, 2H, H-2); 3.77 (s, 2H, CH$_2$CO); 4.32 (ABdq, 2H, H-10); 4.95 (d, 1H, H-6); 5.50 (q, 1H, H-7); 6.93–7.52 (m, 6H, H—Ar); 8.67 (t, 1H, C$^{10}$—NH); 9.03 (d, 1H, C$^7$—NH).
Yield: 65%.

EXAMPLE 7

2.72 g. of 7-ACA were suspended in 150 ml. of anhydrous acetonitrile and 56.8 g. of boron trifluoride etherate were added. The reaction mixture was stirred at 40° C. for 5 hours. The solvent was evaporated in vacuo and the residue was taken up with 200 ml. of water. The pH of the solution was adjusted by 7 by adding potassium phosphate solution and the mixture was diluted with 100 ml. of acetone. 16.9 g. of chloroacetyl chloride dissolved in 80 ml. of anhydrous acetone were added to the solution dropwise at a temperature of 0° to 5° C. and during the addition the pH of the mixture was maintained between 7 and 8. After the mixture was stirred for two further hours at 25° C. and at a pH of 7 to 8 the reaction was accomplished. The pH of the reaction mixture was adjusted to 5 by adding diluted sulphuric acid and the solution was extracted with 300 ml. of ethyl acetate. The pH of the aqueous phase was adjusted to 2 and it was extracted with 600 ml. of ethyl acetate. The organic extract was dried over magnesium sulphate. The solvent was evaporated in vacuo, the residue was treated with ether, washed and dried. 25 g. of 7-chloroacetylamino-3-acetylaminomethylceph-3-em-4-carboxylic acid were obtained.

M.p.: 192°–196° C. (decomp.)

$R_f$: 0.34

$^1$H-NMR ($\delta$ ppm) DMSO-d$_6$: 1.08 (s, 3H, —CH$_3$); 3.47 (ABq, 2H, H-2); 4.05 (ABdq, 2H, H-10); 4.17 (s, 2H, Cl—CH$_2$—); 5.07 (d, 1H, H-6); 5.67 (q, 1H, H-7); 8.13 (t, 1H, C$^{10}$—NH); 9.22 (d, 1H, C$^7$—NH);

Yield: 71.7%.

EXAMPLE 8

1.75 g. of 7-chloroacetylamino-3-acetylaminomethyl-ceph-3-em-4-carboxylic acid and 0.42 g. of sodium hydrocarbonate were dissolved in 10 ml. of water. Thereafter 0.9 g. of 2-phenyl-5-mercapto-1,3,4-oxadiazole and 0.42 g. of sodium hydrocarbonate dissolved in a mixture of 10 ml. of water and 5 ml. of acetone were added. The reaction mixture was stirred at room temperature for 12 hours. The acetone was evaporated in vacuo. The pH of the residue was adjusted to 2 by adding some diluted sulphuric acid. The precipitate separated was removed by filtration and dried. Thus 1.83 g. of 7-(2-phenyl-1,3,4-oxadiazole-5-ylthio)acetylamino-3-acetylaminomethyl-ceph-3-em-4-carboxylic acid were obtained.

M.p.: 170°–174° C. (decomp.)

$R_f$: 0.2

$^1$H-NMR ($\delta$ ppm) DMSO-d$_6$: 1.90 (s, 3H, —CH$_3$); 3.38 (ABq, 2H, H-2); 4.05 (ABdq, 2H, H-10); 4.25 (s, 2H, S—CH$_2$—); 5.06 (d, 1H, H-6); 5.70 (q, 1H, H-7); 7.60–8.00 (m, 5H, H—Ar); 8.15 (t, 1H, C$^{10}$—NH); 9.35 (d, 1H, C$^7$—NH).

Yield: 75%.

EXAMPLE 9

1.96 g. of 7-bromoacetylamino-3-acetylaminomethyl-ceph-3-em-4-carboxylic acid and 1.45 g. of 2-(4-chlorophenoxymethyl)-5-mercapto-1,3,4-oxadiazole were dissolved in 20 ml. of anhydrous dimethyl formamide and 1.52 g. of calcinated potassium carbonate were added thereto. The reaction mixture was stirred at ambient temperature for 8 hours. 50 ml. of ether were added, the precipitate was filtered off and dissolved in 50 ml. of water. The pH of the solution was adjusted to 5 by adding some diluted sulphuric acid and then it was extracted with 30 ml. of ethyl acetate. The pH of the aqueous phase was adjusted to 2 by adding some diluted sulphuric acid and the mixture was extracted with 60 ml. of ethyl acetate. The organic extract was dried over magnesium sulphate. The solvent was evaporated in vacuo and the residue was treated with ether. Thus 2.07 g. of 7-[2-(4-chlorophenoxymethyl)-1,3,4-oxadiazole-5-ylthio]-acetamido-3-acetylaminomethylceph-3-em-4-carboxylic acid were obtained.

M.p.: 115° C. (decomp.)

$R_f$: 0.48

$^1$H-NMR ($\delta$ ppm) DMSO-d$_6$: 1.87 (s, 3H, —CH$_3$); 3.45 (ABq, 2H, H-2); 4.02 (ABdq, 2H, H-10); 4.18 (s, 2H, —S—CH$_2$); 5.05 (d, 1H, H-6); 5.22 (s, 2H, O—CH$_2$); 5.62 (q, 1H, H-7); 7.07–7.40 (AA'XX'm, 4H, H—Ar); 8.12 (t, 1H, C$^{10}$—NH); 9.29 (d, 1H, C$^7$—NH).

Yield: 75%.

EXAMPLE 10

1.0 g. of 7-bromoacetamido-3-acetylaminomethyl-ceph-3-em-4-carboxylic acid, 0.23 g. of 2-amino-5-mercapto-1,3,4-thiadiazole and 0.7 g. of calcinated potassium carbonate were dissolved in 10 ml. of anhydrous dimethyl formamide. The reaction mixture was stirred at room temperature for 2 hours. 30 ml. of diethyl ether were added, the precipitate separated was filtered off and the product was recrystallized from aqueous acetone. Thus 0.78 g. of the potassium salt of 7-(2-amino-1,3,4-thiadiazole-5-ylthio)acetamido-3-acetylaminomethylceph-3-em-4-carboxylic acid were obtained.

M.p.: 243°–245° C. (decomp.)

$R_f$: 0.24

$^1$H-NMR ($\delta$ ppm) DMSO-d$_6$: 1.82 (s, 3H, —CH$_3$); 3.30 (ABq, 2H, H-2); 3.87 (s, 2H, S—CH$_2$—); 4.02 (ABdq, 2H H-10); 4.91 (d, 1H H-6); 5.47 (q, 1H, H-7); 7.47 (s, 2H, —NH$_2$); 7.88 (t, 1H, C$^{10}$—NH); 9.06 (d, 1H, C$^7$—NH).

Yield: 67%.

EXAMPLE 11

Similarly to the process of Example 10 the potassium salt of 7-(1-amino-2-phenyl-1,3,4-triazole-5-ylthio)acetamido-3-acetylaminomethylceph-3-em-4-carboxylic acid was prepared by starting from 7-bromoacetamido-3-acetylaminomethylceph-3-em-4-carboxylic acid and 1-amino-2-phenyl-5-mercapto-1,3,4-triazole.

M.p.: 126°–127° C.

$R_f$: 0.41

$^1$H-NMR ($\delta$ ppm) DMSO-d$_6$: 1.85 (s, 3H—CH$_3$); 3.45 (ABq, 2H, H-2); 4.02 (ABdq, 2H, H-10); 4.07 (s, 2H, S—CH$_2$); 5.06 (d, 1H, H-6); 5.67 (q, 1H, H-7); 7.50 (s, 2H, —NH$_2$); 7.52–7.96 (m, 5H, H—Ar); 8.15 (t, 1H, C$^{10}$—NH); 9.30 (d, 1H, C$^7$—NH).

Yield: 65%.

EXAMPLE 12

1.0 g. of 7-bromoacetamido-3-acetylaminomethyl-ceph-3-em-4-carboxylic acid, 0.3 g. of 1-methyl-5-mercapto-1H-tetrazole and 9.1 g. of triethyl amine were dissolved in 20 ml. of anhydrous dimethyl formamide. The reaction mixture was stirred at room temperature for 12 hours. First 0.7 g. of calcinated potassium carbonate, then 30 ml. of ether were added to the reaction mixture. The precipitate separated was filtered off, dissolved in water, the pH of the solution was adjusted to 2 by adding diluted sulphuric acid and the mixture was extracted with ethyl acetate. The organic extract was dried over anhydrous magnesium sulphate. The solvent was evaporated in vacuo and the residue was treated with diethyl ether. Thus 0.76 g. of 7-(1-methyl-1H-tetrazole-5-ylthio)-acetamido-3-acetylaminomethylceph-3-em-4-carboxylic acid were obtained.

M.p.: 170°–174° C. (decomp.)

$R_f$: 0.35

$^1$H-NMR ($\delta$ ppm) DMSO-d$_6$: 1.83 (s, 3H, —CH$_3$); 3.47 (ABq, 2H, H-2); 3.97 (s, 3H, N—CH$_3$); 4.02 (ABdq, 2H, H-10); 4.13 (s, 2H, —S—CH$_2$—); 5.05 (d, 1H-H-6); 5.65 (q, 1H, H-7); 8,12 (t, 1H, C$^{10}$—NH); 9.24 (d, 1H, C$^7$—NH).

Yield: 71%.

EXAMPLE 13

13.6 g. of 7-ACA were dissolved in 95 ml. of trifluoroacetic acid, then 28.40 g. of boron trifluoride etherate and 12.0 g. of 2,6-dichlorobenzoyl nitrile were added. The reaction mixture was stirred at 50° C. for 5 hours. The solvent was evaporated in vacuo and the residue was suspended in 50 ml. of water. The pH of the suspension was adjusted to 3.5 by adding sodium hydroxide solution and the precipitate separated was removed by filtration. 13–15 g. of the solid substance obtained and 8 g. of sodium hydrocarbonate were dissolved in a mixture of 200 ml. of water and 200 ml. of acetone. 8 g. of bromoacetyl chloride dissolved in 20 ml. of anhydrous acetone were added to the solution dropwise at 0° to 5° C., while the pH of the reaction mixture was maintained between 7 and 8 by adding a solution of potassium phosphate. When stirring the mixture at 25° C. at pH 8 for 2 further hours the reaction was accomplished. The pH of the reaction mixture was adjusted by 5 by adding a diluted solution of sulphuric acid and the solution was extracted with 300 ml. of ethyl acetate. The organic extract was dried over magnesium sulphate. The solvent was evaporated in vacuo, the residue was treated with ether, filtered and dried. 13.9 g. of 7-bromoacetamido-3-(2,6-dichlorobenzoylamino)methylceph-3-em-4-carboxylic acid were obtained in powder form (53%).

M.p.: 110°–113° C. (decomp.)

$R_f^2$: 0.58

$^1$H-NMR (δ ppm) DMSO-d$_6$: 3.60 (ABq, 2H, H-2); 4.17 (s, 2H, Br—CH$_2$); 4.32 (ABdq, 2H, H-10); 5.11 (d, 1H, H-6); 5.65 (q, 1H, H-7); 7.32–7.57 (m, 3H, H—Ar); 9.27 (d, 1H, C$^7$—NH).

Yield: 53%.

EXAMPLE 14

1.0 g. of 7-bromoacetamido-3-(2,6-dichlorobenzoylamino)methylceph-3-em-4-carboxylic acid, 0.23 g. of 1-methyl-5-mercapto-1H-tetrazole and 9.1 g. of triethylamine were dissolved in 10 ml. of anhydrous acetone. The reaction mixture was stirred at room temperature for 4 hours. Working up the solution 10 ml. of water were added, the pH was adjusted to 2 by adding a solution of diluted sulphuric acid and the mixture was extracted with 30 ml. of ethyl acetate. The organic extract was dried over magnesium sulphate. The solvent was evaporated under vacuo and the residue was treated with ether and dried. 0.7 g. (62%) of 7-(1-methyl-1H-tetrazole-5-ylthio)acetamido-3-(2,6-dichlorobenzamino)methylceph-3-em-4-carboxylic acid were obtained.

M.p.: 154°–156° C. (decomp.)

$R_f^2$: 0.56

$^1$H-NMR (ppm) DMSO-d$_6$: 3.58 (ABq, 2H, H-2); 4.00 (s, 3H, N—CH$_3$); 4.17 (s, 2H, S—CH$_2$); 4.30 (ABdq, 2H, H-10); 5.10 (d, 1H, H-6); 5.67 (q, 1H-H-7); 7.42–7.55 (m, 3H, H—Ar); 9.00 (t, 1H, C$^{10}$—NH); 9.27 (d, 1H, C$^7$—NH).

Yield: 62%.

EXAMPLE 15

1.0 g. of 7-bromoacetamido-3-(2,6-dichlorobenzoylamino)methylceph-3-em-carboxylic acid and 0.36 g. of 2-phenyl-5-mercapto-1,3,4-oxadiazole were dissolved in 10 ml. of dimethyl formamide and 0.28 g. of calcinated potassium carbonate were added. The reaction mixture was stirred at room temperature for 8 hours, 30 ml. of ether were added, the precipitate was filtered off and dissolved in 30 ml. of water. The solution was adjusted to pH 5 by adding dilute sulphuric acid and extracted with 20 ml. of ethyl acetate. The aqueous layer was adjusted to pH 2 by adding dilute sulphuric acid and extracted with 60 ml. of ethyl acetate. The organic extract was dried over magnesium sulphate. The solvent was evaporated in vacuo and the residue was treated with ether and dried. 0.72 g. of 7-(2-phenyl-1,3,4-oxadiazole-5-ylthio)acetamido-3-(2,6-dichlorobenzoylamino)methylceph-3-em-4-carboxylic acid were obtained.

M.p.: 178°–180° C. (decomp.)

$R_f^2$: 0.68

$^1$H-NMR (δ ppm) DMSO-d$_6$: 3.56 (ABq, 2H, H-2); 4.24 (s, 2H, S—CH$_2$); 4.30 (ABdq, 2H, H-10); 5.10 (d, 1H, H-6); 5.70 (q, 1H, H-7); 7.35–8.02 (m, 8H, H—Ar); 9.00 (t, 1H, C$^{10}$—NH); 9.38 (d, 1H, C$^7$—NH).

Yield: 58%.

EXAMPLE 16

1.0 g. of 7-bromoacetamido-3-(2,6-dichlorobenzoylamino)methylceph-3-em-4-carboxylic acid and 0.39 g. of 2-mercapto-4-phenyl-1,3-thiazole were reacted and worked up according to the method of Example 15. Thus 0.78 g. o(62%) of 7-(4-phenyl-1,3-thiazole-2-ylthio)acetamido-3-(2,6-dichlorobenzoylamino)methylceph-3-em-4-carboxylic acid were obtained.

$^1$H-NMR (δ ppm) DMSO-d$_6$: 3.47 (ABq, 2H, H-2); 4.07 (s, 2H, S—CH$_2$—); 4.32 (ABdq, 2H, H-10); 4.95 (d, 1H-H-6); 5.50 (q, 1H, H-7); 5.83 (s, 1H, H S); 7.2–7.5 (m, 5H, H—Ar); 8.67 (t, 1H, C$^{10}$—NH); 9.03 (d, 1H, C$^7$—NH).

Yield: 62%.

EXAMPLE 17

1.0 g. of 7-bromoacetamido-3-(2,6-dichlorobenzoylamino)methylceph-3-em-4-carboxylic acid and 0.23 g. of 1-methyl-2-mercapto-imidazole were reacted and worked up according to Example 15. Thus 0.67 g. (60%) of 7-(1-methylimidazole-2-ylthio)-acetamido-3-(2,6-dichlorobenzoylamino)methylceph-3-em-4-carboxylic acid were obtained.

$^1$H-NMR (δ ppm) DMSO-d$_6$: 3.45 (ABq, 2H, H-2); 4.00 (s, 3H, N—CH$_3$); 4.02 (ABdq, 2H-H10); 4.15 (s, 2H, —S—CH$_2$—); 4.92 (d, 1H, H-6); 5.60 (q, 1H, H-7); 7.10–7.30 (m, 2H, H—Ar); 8.65 (t, 1H, C$^{10}$—NH); 9.04 (d, 1H, C$^7$—NH).

Yield: 60%.

EXAMPLE 18

1.0 g. of 7-bromoacetamido-3-(2,6-dichlorobenzoylamino)methylceph-3-em-4-carboxylic acid and 0.24 g. of 5-mercapto-1,2,3,4-thiatriazole were reacted and worked up according to the method of Example 15. Thus 0.73 g. (65%) of 7-(1,2,3,4-thiatriazole-5-ylthio)-acetamido-3-(2,6-dichlorobenzoylamino)methylceph-3-em-4-carboxylic acid were obtained.

$^1$H-NMR (δ ppm) DMSO-d$_6$: 3.49 (ABq, 2H, H-2); 4.05 (s, 2H, —S—CH$_2$); 4.35 (ABdq, 2H, H-10); 4.95 (d, 1H, H-6); 5.52 (q, 1H, H-7); 8.67 (t, 1H, C$^{10}$—NH); 9.03 (d, 1H, C$^7$—NH).

Yield: 65%.

What we claim is:

1. 7-(2-thienyl)acetylamino-3-(4-chlorophenylacetylamino)-methyl-ceph-3-ene-4-carboxylic acid or an alkali metal carboxylate salt thereof.

2. 7-(2-thienyl)-acetylamino-3-(2,6-dichlorobenzoylamino)-methyl-ceph-3-ene-4-carboxylic acid or an alkali metal carboxylate salt thereof.

* * * * *